United States Patent
Tsai et al.

(10) Patent No.: US 9,778,200 B2
(45) Date of Patent: Oct. 3, 2017

(54) METHOD AND APPARATUS FOR ANALYTE MEASUREMENT

(71) Applicant: IXENSOR CO., LTD., Taipei OT (TW)

(72) Inventors: Tungmeng Tsai, Taipei (TW); Yenyu Chen, Taipei (TW); Chieh Hsiao Chen, Taipei (TW)

(73) Assignee: IXENSOR CO., LTD. (TW)

( * ) Notice: Subject to any disclaimer, the term of this patent is extended or adjusted under 35 U.S.C. 154(b) by 621 days.

(21) Appl. No.: 13/941,563

(22) Filed: Jul. 15, 2013

(65) Prior Publication Data

US 2014/0170757 A1 Jun. 19, 2014

Related U.S. Application Data

(60) Provisional application No. 61/739,005, filed on Dec. 18, 2012.

(51) Int. Cl.
| | |
|---|---|
| *G01N 35/08* | (2006.01) |
| *G01N 21/78* | (2006.01) |
| *G01N 21/84* | (2006.01) |
| *G01N 21/29* | (2006.01) |

(52) U.S. Cl.
CPC ......... *G01N 21/78* (2013.01); *G01N 21/8483* (2013.01); *G01N 21/293* (2013.01); *G01N 2201/0221* (2013.01); *Y10T 436/12* (2015.01)

(58) Field of Classification Search
None
See application file for complete search history.

(56) References Cited

U.S. PATENT DOCUMENTS

| | | | |
|---|---|---|---|
| 5,011,290 | A | 4/1991 | Terada et al. |
| 5,077,010 | A | 12/1991 | Ishizaka et al. |
| 5,277,870 | A | 1/1994 | Fuller et al. |
| 5,281,395 | A | 1/1994 | Markart et al. |
| 5,408,535 | A | 4/1995 | Howard, III et al. |
| 5,556,761 | A | 9/1996 | Phillips |
| 5,719,034 | A | 2/1998 | Kiser et al. |
| 5,843,691 | A | 12/1998 | Douglas et al. |
| 6,168,957 | B1 | 1/2001 | Matzinger et al. |

(Continued)

FOREIGN PATENT DOCUMENTS

| | | |
|---|---|---|
| CA | 2601720 A1 | 10/2006 |
| CA | 2601720 C | 8/2014 |

(Continued)

OTHER PUBLICATIONS

Iqbal, Z. et al. Spectral Fingerprinting on a StandardMobile Phone, 2010, Journal of Sensors, vol. 2010, p. 1-9.*

(Continued)

*Primary Examiner* — Robert Xu
(74) *Attorney, Agent, or Firm* — SU IP Consulting

(57) ABSTRACT

A method is provided for a portable computing device to read a reaction area on a test strip, which is located in a peripheral device placed over an image sensor and a light source of the portable computing device. Light is provided with the light source, which the peripheral device directs to the reaction area. An image including the reaction area is captured with the image sensor. An analyte characteristic is determined based on a color of the captured reaction area in the image.

18 Claims, 14 Drawing Sheets

(56) References Cited

U.S. PATENT DOCUMENTS

| | | | |
|---|---|---|---|
| 6,494,830 | B1 | 12/2002 | Wessel |
| 6,531,322 | B1 | 3/2003 | Jurik et al. |
| 6,572,822 | B2 | 6/2003 | Jurik et al. |
| 6,602,469 | B1 | 8/2003 | Maus et al. |
| 6,770,487 | B2 * | 8/2004 | Crosby .............. G01N 33/558 422/547 |
| 7,267,799 | B1 | 9/2007 | Borich et al. |
| 7,767,149 | B2 | 8/2010 | Maus et al. |
| 7,988,845 | B2 | 8/2011 | Heller et al. |
| 8,145,431 | B2 | 3/2012 | Kloepfer et al. |
| 8,257,654 | B2 | 9/2012 | Maus et al. |
| 8,935,007 | B2 | 1/2015 | Kloepfer et al. |
| 9,023,295 | B2 * | 5/2015 | Chumanov ........... G01J 3/0291 422/561 |
| 9,063,091 | B2 | 6/2015 | Tsai et al. |
| 2002/0006355 | A1 | 1/2002 | Whitson |
| 2002/0098114 | A1 | 7/2002 | Harding et al. |
| 2005/0203353 | A1 | 9/2005 | Ma et al. |
| 2006/0024835 | A1 | 2/2006 | Matzinger et al. |
| 2006/0222567 | A1 | 10/2006 | Kloepfer et al. |
| 2006/0292039 | A1 * | 12/2006 | Iida ..................... A61B 5/0002 422/82.05 |
| 2007/0279328 | A1 | 12/2007 | Takada et al. |
| 2008/0019867 | A1 * | 1/2008 | Johnson .............. A61B 10/007 422/400 |
| 2008/0309939 | A1 | 12/2008 | Sugawara |
| 2009/0098657 | A1 | 4/2009 | Blais et al. |
| 2009/0154776 | A1 * | 6/2009 | Mott ..................... G01N 21/75 382/110 |
| 2010/0216175 | A1 | 8/2010 | Melker et al. |
| 2011/0190607 | A1 | 8/2011 | Matzinger et al. |
| 2012/0010489 | A1 | 1/2012 | Miltner et al. |
| 2012/0045842 | A1 | 2/2012 | Petrich et al. |
| 2012/0089051 | A1 | 4/2012 | Draudt et al. |
| 2012/0183442 | A1 | 7/2012 | Kloepfer et al. |
| 2012/0189509 | A1 | 7/2012 | Hsiao |
| 2012/0194457 | A1 | 8/2012 | Cannon et al. |
| 2012/0201755 | A1 | 8/2012 | Rozakis et al. |
| 2013/0041691 | A1 | 2/2013 | Maus et al. |
| 2015/0254844 | A1 | 9/2015 | Tsai et al. |
| 2015/0254845 | A1 | 9/2015 | Tsai et al. |

FOREIGN PATENT DOCUMENTS

| | | |
|---|---|---|
| CN | 101401000 A | 4/2009 |
| CN | 101715555 A | 5/2010 |
| CN | 102203574 A | 9/2011 |
| CN | 102841197 A | 12/2012 |
| EP | 0851229 A1 | 7/1998 |
| EP | 1621887 A1 | 2/2006 |
| EP | 1866637 A2 | 12/2007 |
| EP | 1866637 A4 | 7/2013 |
| GB | 2483482 A | 3/2012 |
| JP | H01-138458 A | 5/1989 |
| JP | H06-012961 A | 6/1992 |
| JP | H09-101305 A | 4/1997 |
| JP | H09-105750 A | 4/1997 |
| JP | 2005-172533 A | 6/2005 |
| JP | 2007-506077 A | 3/2007 |
| JP | 2007-101482 A | 4/2007 |
| JP | 2009-020026 A | 1/2009 |
| TW | 201018907 A | 5/2010 |
| WO | 2005088519 A1 | 9/2005 |
| WO | 2006107666 A2 | 10/2006 |
| WO | 2006107666 A3 | 6/2007 |
| WO | 2010081219 A1 | 7/2010 |
| WO | 2012032171 A1 | 3/2012 |
| WO | 2012131386 A1 | 10/2012 |
| WO | 2013093454 A1 | 6/2013 |

OTHER PUBLICATIONS

"HealthPia GlucoPhone", retrieved from the internet at <URL: www.diabetesnet.com/healthpia-glucophone> on Jul. 8, 2013.

"Important Information Regarding the iBGStar Diabetes Manager Application-version2.0", retrieved from the internet at <URL: www.bgstar.com/web/ibgstar> on Jul. 8, 2013.

International Search Report and Written Opinion of The International Searching Authority, International application No. PCT/CN2013/081138, Nov. 21, 2013.

The Extended European Search Report, Application No. EP 13864973.6, dated Sep. 30, 2016.

David J. You et al., "Cell-Phone Based Measurement of TSH Using Mie Scatter Optimized Lateral Flow Assays", Biosensors and Bioelectronics, 2013, pp. 180-185, vol. 40.

Marina Velikova et al., "Fully-Automated Interpretation of Biochemical Tests for Decision Support by Smartphones", IEEE, 2012.

International Search Report and Written Opinion of the International Searching Authority, International application No. PCT/CN2013/074229, dated Jul. 18, 2013.

The Extended European Search Report, EP 13771998.5, dated Jul. 22, 2016.

Nicola Dell et al., "Towards a Point-of-Care Diagnostic System: Automated Analysis of Immunoassay Test Data on a Cell Phone", Jun. 28, 2011, NSDR'11, Bethesda, Maryland, USA.

David J. You et al., "Cell-Phone-Based Measurement of TSH Using Mie Scatter Optimized Lateral Flow Assays", Biosensors and Bioelectronics, 2013, pp. 180-185, vol. 40.

* cited by examiner

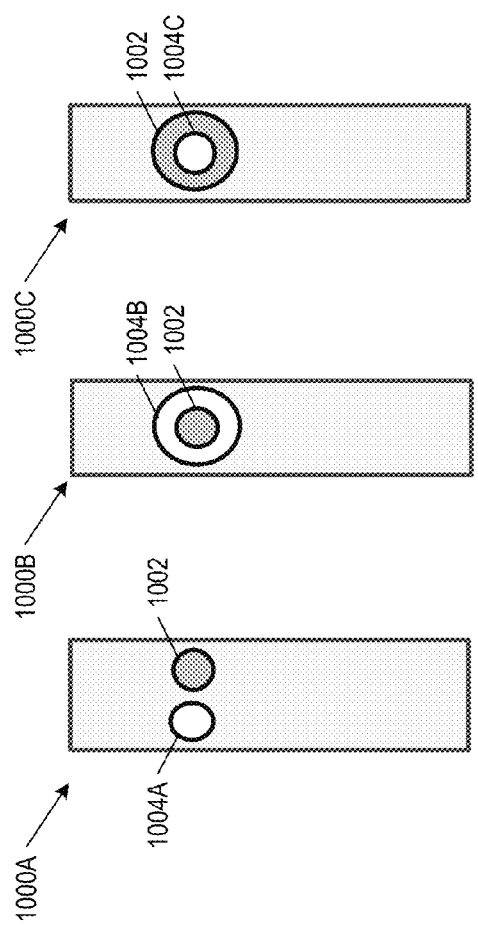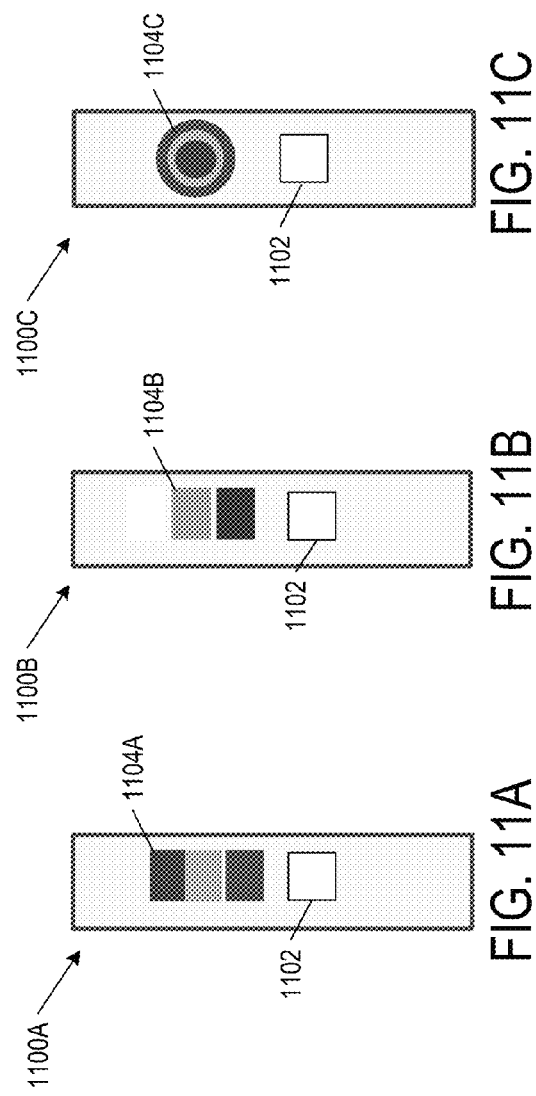

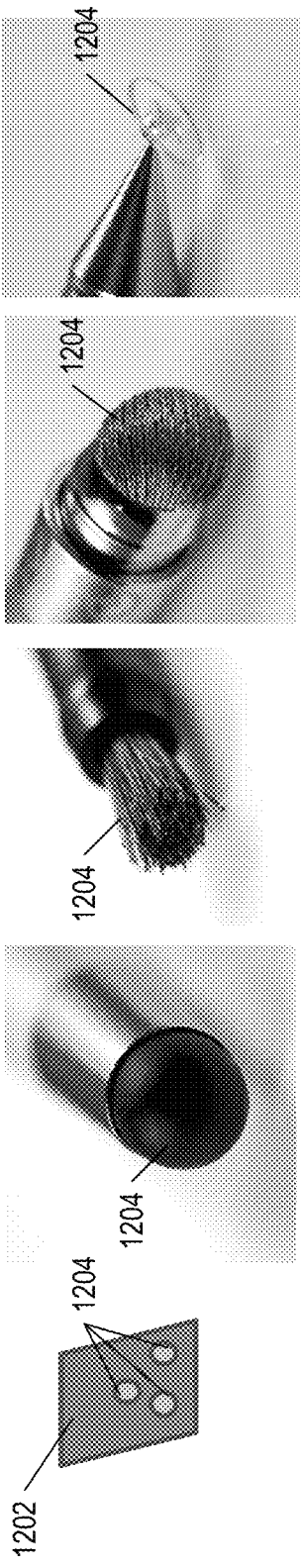
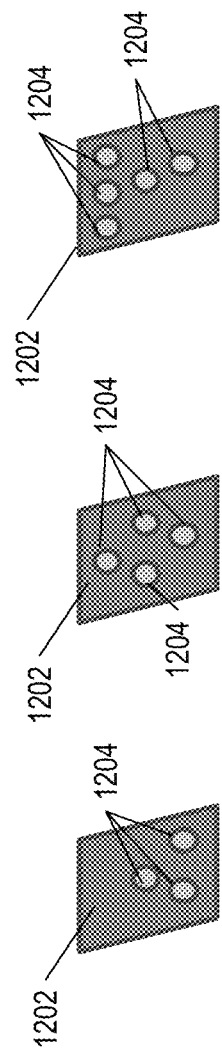
FIG. 12A  FIG. 12B  FIG. 12C  FIG. 12D  FIG. 12E
FIG. 13A  FIG. 13B  FIG. 13C

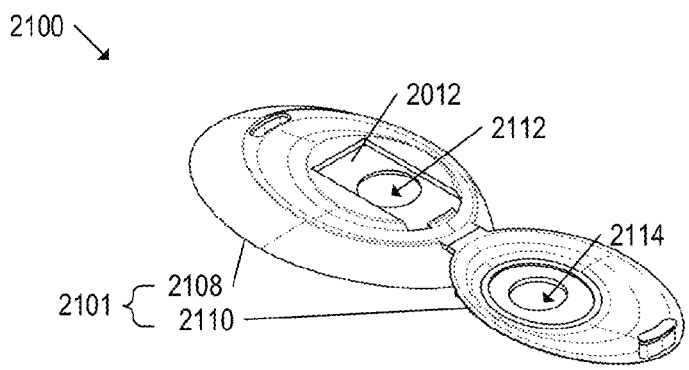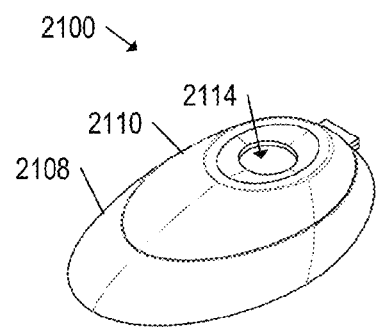
FIG. 21A  FIG. 21B
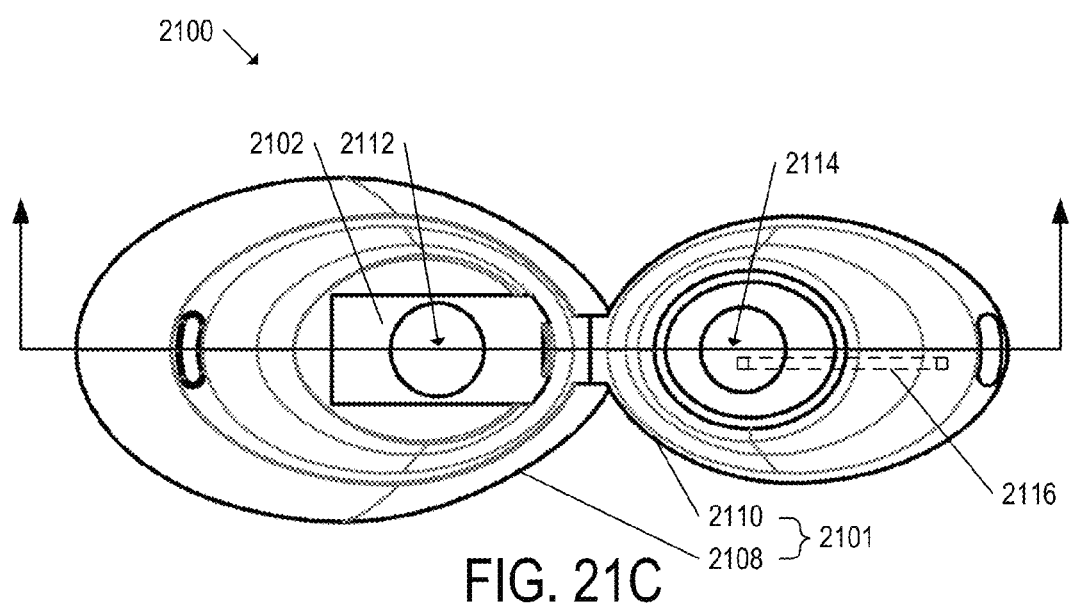
FIG. 21C
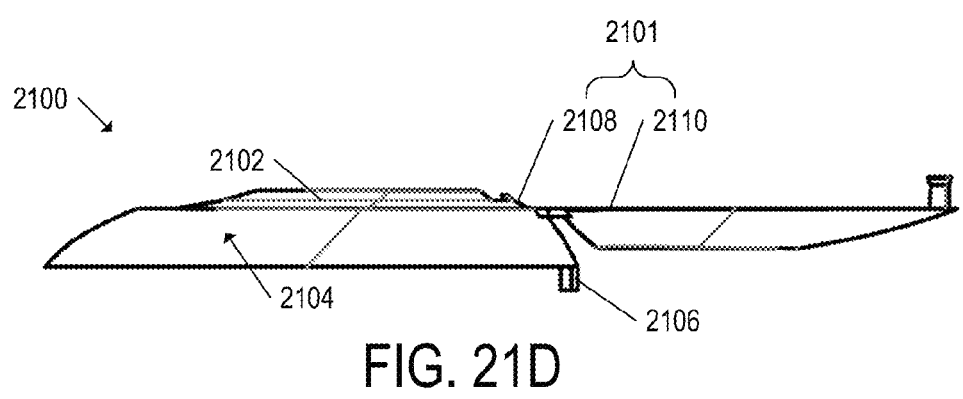
FIG. 21D

US 9,778,200 B2

METHOD AND APPARATUS FOR ANALYTE MEASUREMENT

CROSS-REFERENCE TO RELATED APPLICATIONS

This application claims the benefit of U.S. Provisional Application No. 61/739,005, filed Dec. 18, 2012, which is incorporated by reference in its entirety.

This application is related to U.S. patent application Ser. No. 13/798,175, filed Mar. 13, 2013, now U.S. Pat. No. 9,063,091, which is incorporated by reference in its entirety.

FIELD

The present disclosure generally relates to methods and systems for analyte measurement.

BACKGROUND

FIG. 1 shows a specimen test strip 100 with a reaction area 102. Reaction area 102 contains reagents that react with an analyte in a specimen sample, such as glucose in a blood sample. When the specimen sample reaches reaction area 102, reaction area 102 changes color according to a characteristic of the analyte, such as the glucose level in blood. The user visually compares the color of reaction area 102 against a chart 104 to correlate the color of reaction area 102 to the characteristic of the analyte. Alternatively the user inserts specimen test strip 100 into a meter, which optically determines the characteristic of the analyte.

SUMMARY

According to aspects of the present disclosure, a method is provided for a portable computing device to read a reaction area on a test strip, which is located in a test strip peripheral device placed over an image sensor and a light source of the portable computing device. Light is provided with the light source, which the peripheral device directs to the reaction area. An image including the reaction area is captured with the image sensor. An analyte characteristic is determined based on a color of the captured reaction area in the image.

According to other aspects of the present disclosure, a test strip peripheral device is to be placed over an image sensor and a light source of a portable computing device to assist the portable computing device in reading a reaction area on a test strip in the peripheral device. The peripheral device includes a light guide to direct light from the light source to the test strip, and an alignment feature to aid the placement of the peripheral device relative to the image sensor and the light source on the portable computing device.

According to other aspects of the present disclosure, a test strip is to detect an analyte characteristic in a specimen sample. The test strip includes a reaction area to receive the specimen sample, and conductive smart dots to be detected by a touchscreen. Information about the test strip is conveyed based on an arrangement of the smart dots, an orientation of the smart dots, or both.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are therefore not to be considered limiting of its scope, the disclosure will be described with additional specificity and detail through use of the accompanying drawings.

In the drawings:

FIGS. 10A, 10B, and 10C show test strips with reaction and reference areas in examples of the present disclosure;

FIGS. 11A, 11B, and 11C show test strips with reaction and color calibration areas in examples of the present disclosure;

FIG. 12A shows conductive smart dots on a test strip or a test strip peripheral device in examples of the present disclosure;

FIGS. 12B, 12C, 12D, and 12E show different types of smart dots in examples of the present disclosure;

FIGS. 13A, 13B, and 13C show different arrangements of smart dots in examples of the present disclosure;

FIGS. 21A, 21B, 21C, and 21D show first perspective, second perspective, top, and side views of a tenth test strip peripheral device in examples of the present disclosure.

DETAILED DESCRIPTION

As used herein, the term "includes" means includes but not limited to, the term "including" means including but not limited to. The terms "a" and "an" are intended to denote at least one of a particular element. The term "based on" means based at least in part on.

Figure 1:
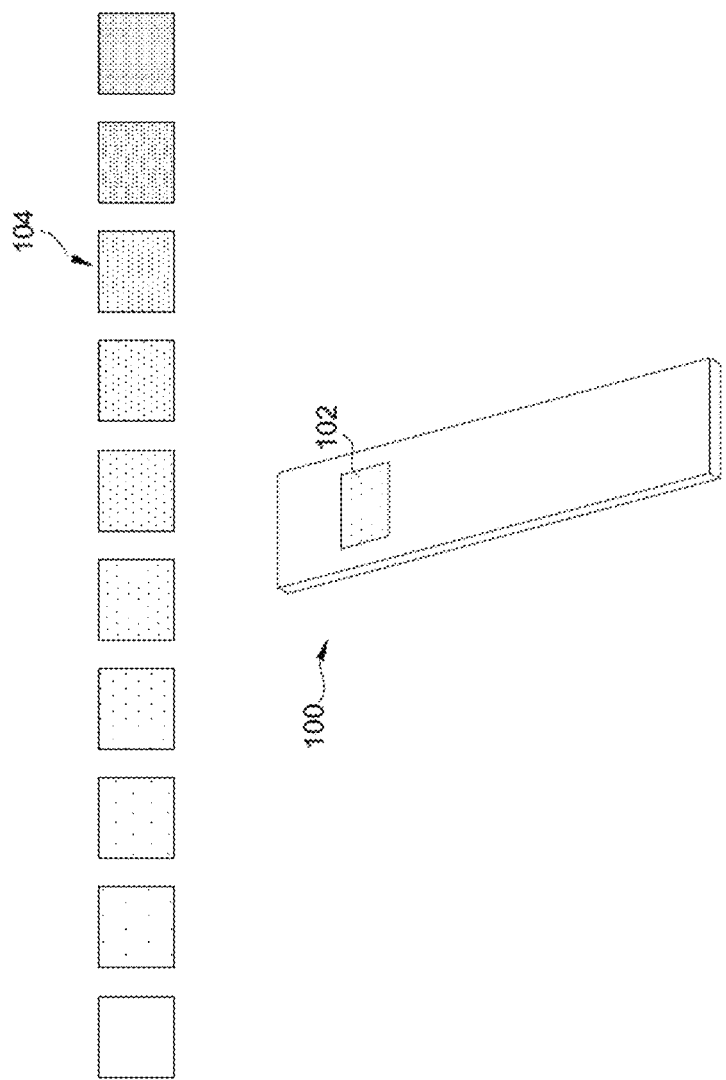
FIG. 1 shows a prior art specimen test strip.
Figure 2A:
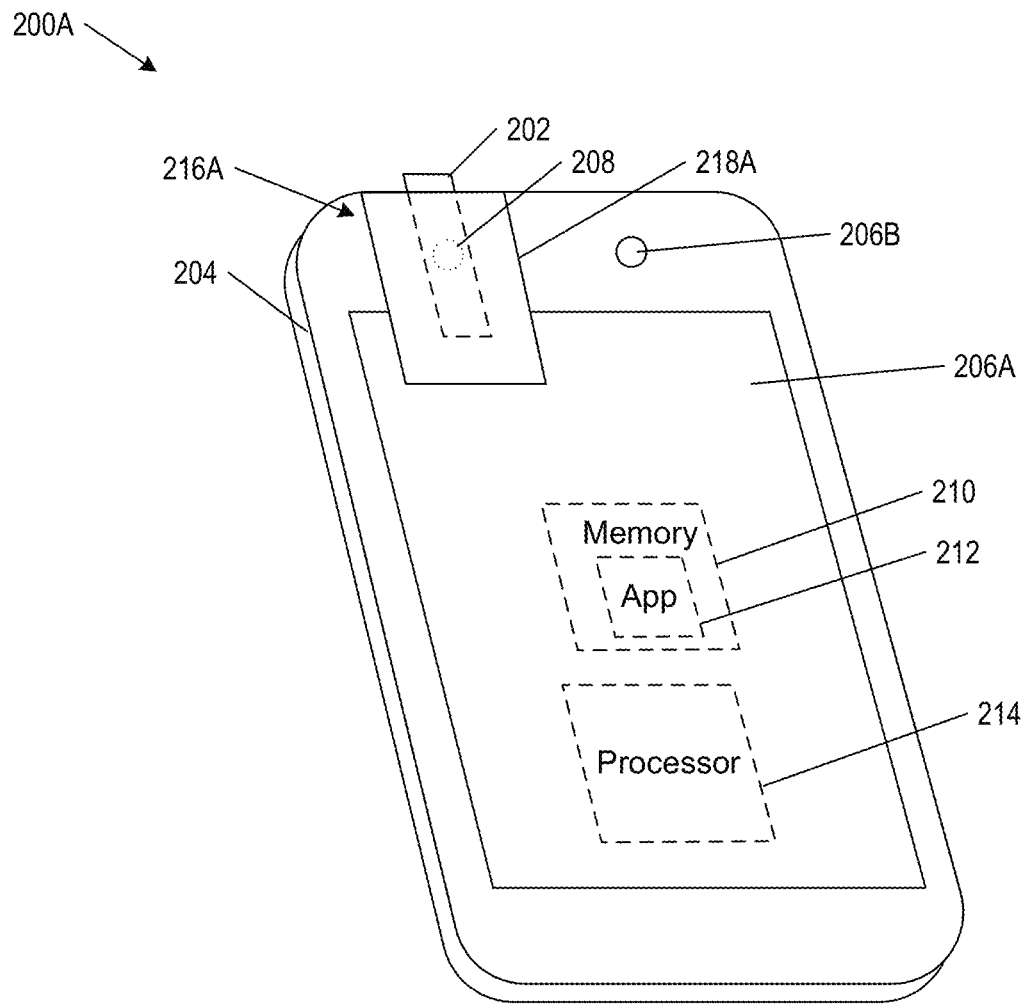
FIGS. 2A and 2B show systems each including a portable computing device and a test strip peripheral device to assist the portable computing device in reading a test strip in examples of the present disclosure.

FIG. 2A shows a system 200A to detect a characteristic of an analyte on a test strip 202 in examples of the present disclosure. System 200A includes a portable computing device 204, such as a smart phone or a tablet computer. Device 204 has a screen 206A (e.g., a touchscreen), a flash 206B, an image sensor 208 (shown in phantom), a non-transitory computer readable medium 210 (shown in phantom) for storing processor executable instructions of an application 212 (shown in phantom), and a processor 214 (shown in phantom) to run the application. Executing application 212, processor 214 illuminates a reaction area on test strip 202 with light from screen 206A, captures an image of the reaction area with image sensor 208, determines the color of the captured reaction area in the image, and determines the analyte characteristic based on the color of the captured reaction area in the image.

System 200A includes a test strip peripheral device 216A that assists device 204 in reading the reaction area on test strip 202. Peripheral device 216A includes a light guide 218A that directs light from screen 206A to the reaction area on test strip 202.

Figure 2B:
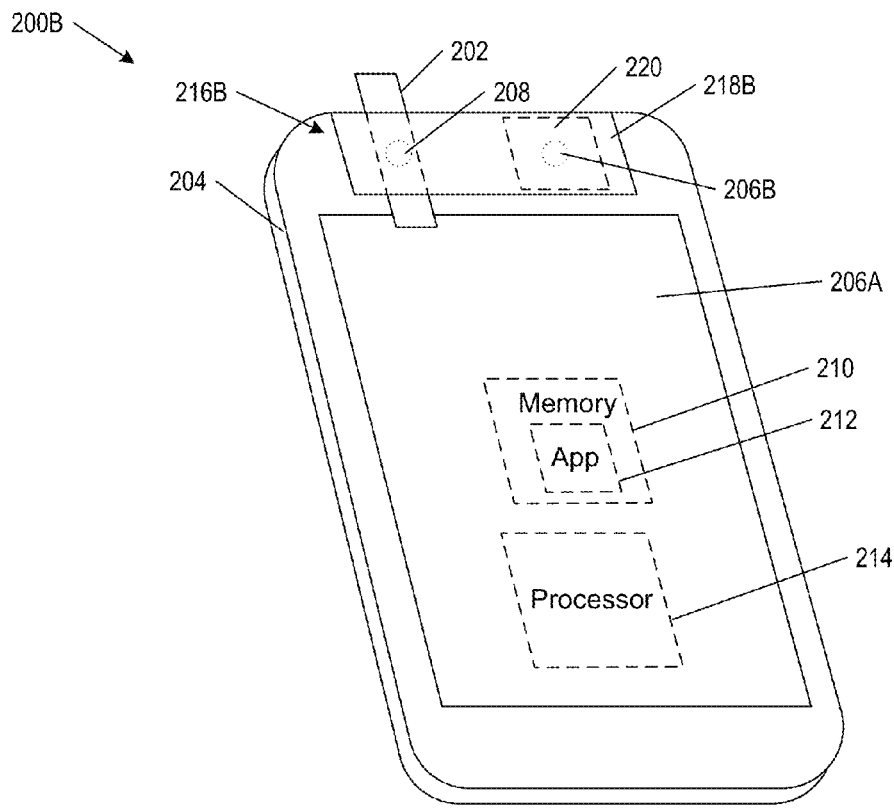

FIG. 2B shows a system 200B to detect a characteristic of an analyte on test strip 202 in examples of the present disclosure. System 200B includes device 204 and a test strip peripheral device 216B. Executing application 212, processor 214 illuminates the reaction area on test strip 202 with light from flash 206B (shown in phantom), captures an image of the reaction area with image sensor 208, determines the color of the captured reaction area in the image, and determines the analyte characteristic based on the color of the captured reaction area in the image.

Peripheral device 216B includes a light guide 218B that directs light from flash 206B to the reaction area on test strip 202. Peripheral device 216B includes a color filter 220 (shown in phantom) to control the color of the light illuminating the reaction area on test strip 202.

Figure 3:
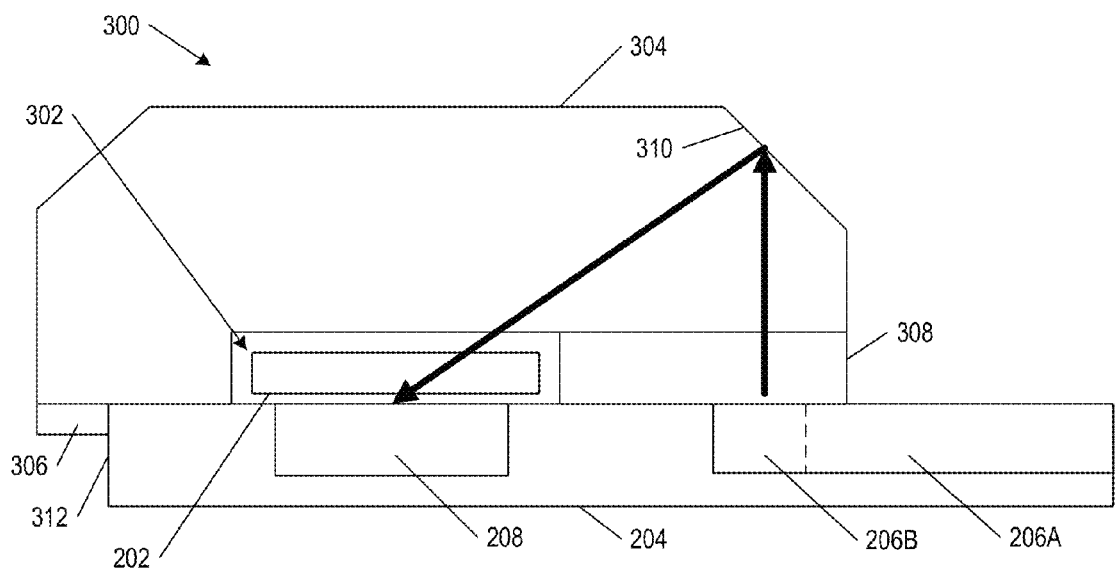
FIG. 3 shows a side view of a first test strip peripheral device for portable computing devices in examples of the present disclosure.

FIG. 3 shows a test strip peripheral device 300 for device 204 in examples of the present disclosure. Peripheral device 300 includes a test strip slot or compartment 302 to receive test strip 202, a light guide 304 to direct light from a light source, such as screen 206A or flash 206B, to the reaction area on the test strip, and an alignment feature 306 to aid the placement of the peripheral device on the portable computing device. When flash 206B is used as the light source, peripheral device 300 includes a color filter 308 to control the color of the light illuminating the reaction area on test strip 202.

Light emits upward from screen 206A or flash 206B, optionally travels through color filter 308, reflects diagonally downward from a reflective surface 310 of light guide 304, passes through the reaction area on test strip 202, and impinges image sensor 208.

In some examples, light guide 304 is a transparent block and reflective surface 310 is a beveled edge of the transparent block that reflects light by total internal reflection (TIR) or a reflective coating. Light guide 304 may be covered in a case or by a coating to prevent ambient light from entering so the reaction area on test strip 202 is illuminated substantially by screen 206A or flash 206B. In other examples light guide 304 is the reflective interior in a hollow case of peripheral device 300 and reflective surface 310 is a surface of the reflective interior. The hollow case blocks ambient light so the reaction area on test strip 202 is illuminated substantially by screen 206A or flash 206B.

Color filter 308 is located above a portion of screen 206A or flash 206B. In other examples color filter 308 is located over test strip 202.

Alignment feature 306 abuts against an edge 312 of device 204 to place test strip 202 above imaging sensor 208 and reflective surface 310 of light guide 304 over a portion of screen 206A or flash 206B. In other examples, alignment feature 306 may be received in an opening on device 204, such as a speaker opening or an earphone jack.

Figure 4:
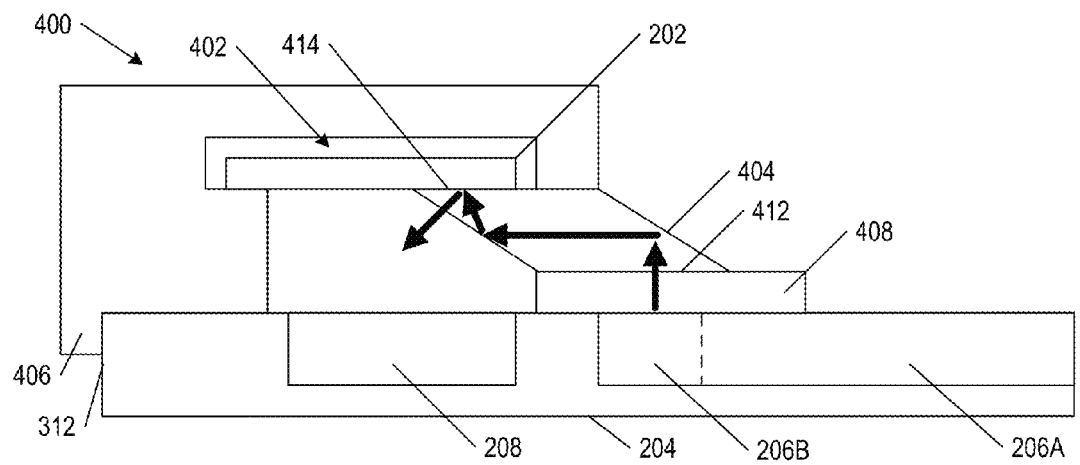
FIG. 4 shows a side view of a second test strip peripheral device for portable computing devices in examples of the present disclosure.

FIG. 4 shows a test strip peripheral device 400 for device 204 in examples of the present disclosure. Peripheral device 400 includes a test strip slot or compartment 402 to receive test strip 202, a light guide 404 to direct light from screen 206A or flash 206B to the reaction area on the test strip, and an alignment feature 406 to aid the placement of the peripheral device on the portable computing device. When flash 206B is used as the light source, peripheral device 400 includes a color filter 408 to control the color of the light illuminating the reaction area on test strip 202.

Light emits from screen 206A or flash 206B, optionally travels through color filter 408, travels from an entrance face 412 of light guide 404 to an exit face 414 of the light guide, reflects diagonally downward from the reaction area on test strip 202, and impinges image sensor 208.

Light guide 404 is slanted so entrance face 412 is located above a portion of screen 206A or flash 208 and exit face 414 is located below the reaction area on test strip 202. In some examples, light guide 404 is a transparent block that constrains light by TIR or a reflective coating on its surfaces. In other embodiments, light guide 404 is hollow and constrains light by a reflective coating on its surfaces. Light guide 404 may be covered in a case or by a coating to prevent ambient light from entering so the reaction area on test strip 202 is illuminated substantially by screen 206A or flash 206B.

Color filter 408 is located above a portion of screen 206A or flash 206B. In other examples color filter 408 is located below the reaction area on test strip 202.

Alignment feature 406 abuts against edge 312 of device 204 to place test strip 202 above imaging sensor 208 and light guide 404 over a portion of screen 206A or flash 206B. In other examples, alignment feature 406 may be received in an opening on device 204, such as a speaker opening or an earphone jack.

Figure 5:
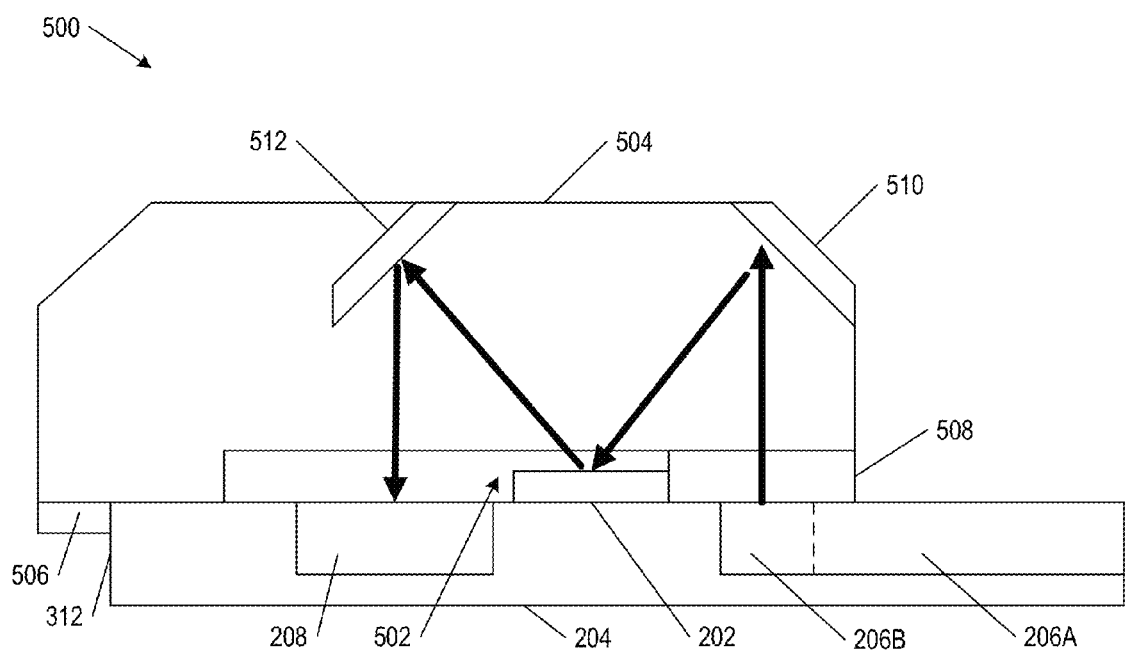
FIG. 5 shows a side view of a third test strip peripheral device for portable computing devices in examples of the present disclosure.

FIG. 5 shows a test strip peripheral device 500 for device 204 in examples of the present disclosure. Peripheral device 500 includes a test strip slot or compartment 502 to receive test strip 202, a light guide 504 to direct light to and from the reaction area to imaging sensor 208, and an alignment feature 506 to aid the placement of the peripheral device on the portable computing device. When flash 206B is used as the light source, peripheral device 500 includes a color filter 508 to control the color of the light illuminating the reaction area on test strip 202.

In some examples, light emits upward from screen 206A or flash 206B, optionally travels through color filter 508, reflects diagonally downward from a first reflective surface 510 of light guide 504, reflects diagonally upward from the reaction area on test strip 202, reflects downward from a second reflective surface 512 of the light guide, and impinges image sensor 208.

In some examples, light guide 504 is a transparent block, first reflective surface 510 is a beveled edge of the transparent block that reflects light by TIR or a reflective coating, and second reflective surface 512 is a reflector embedded in the light guide. Light guide 504 may be covered in a case or by a coating to prevent ambient light from entering so the reaction area on test strip 202 is illuminated substantially by screen 206A or flash 206B. In other examples light guide 504 is the reflective interior in a hollow case of peripheral device 500 and reflective surfaces 510, 512 are surfaces of the reflective interior. The hollow case blocks ambient light so the reaction area on test strip 202 is illuminated substantially by screen 206A or flash 206B.

Color filter 508 is located above a portion of screen 206A or flash 206B. In other examples color filter 508 is located over test strip 202.

Alignment feature 506 abuts against edge 312 of device 204 to place second reflective surface 512 above imaging sensor 208 and first reflective surface 510 over a portion of screen 206A or flash 206B. In other examples, alignment feature 506 may be received in an opening on device 204, such as a speaker opening or an earphone jack.

Figure 6:
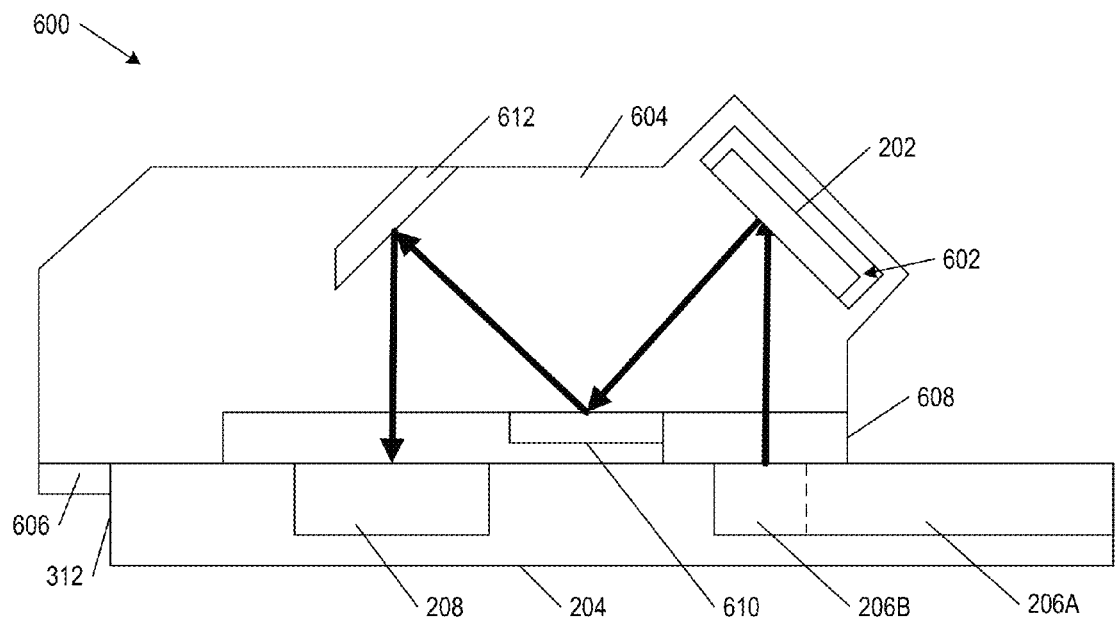
FIG. 6 shows a side view of a fourth test strip peripheral device for portable computing devices in examples of the present disclosure.

FIG. 6 shows a peripheral device 600 for device 204 in examples of the present disclosure. Peripheral device 600 includes a test strip slot or compartment 602 to receive test strip 202, a light guide 604 to direct light to and from the reaction area on the test strip, and an alignment feature 606 to aid the placement of the peripheral device on the portable computing device. When flash 206B is used as the light source, peripheral device 600 includes a color filter 608 to control the color of the light illuminating the reaction area on test strip 202.

Light is emitted upward from light source 206A or flash 206B, optionally travels through color filter 608, reflects diagonally downward from the reaction area on test strip 202, reflects diagonally upward from a first reflective surface 610 of light guide 604, reflects downward from a second reflective surface 612 of the light guide, and impinges image sensor 208.

In some examples, light guide 604 is a transparent block having a beveled edge that forms part of test strip slot or compartment 602. First reflective surface 610 is located on the bottom of light guide 604 and laterally offset from test strip 202. First reflective surface 610 reflects light by TIR or a reflective coating. Second reflective surface 612 is a reflector embedded in light guide 604 and is laterally offset from first reflective surface 610. Light guide 604 may be covered in a case or by a coating to prevent ambient light from entering so the reaction area on test strip 202 is illuminated substantially by screen 206A or flash 206B. In other examples light guide 604 is the reflective interior in a hollow case of peripheral device 600 and reflective surfaces 610 and 612 are surfaces of the reflective interior. The hollow case blocks ambient light so the reaction area on test strip 202 is illuminated substantially by screen 206A or flash 206B.

Color filter 608 is located above a portion of screen 206A or flash 206B.

Alignment feature 606 abuts against edge 312 of device 204 to place test strip 202 over a portion of screen 206A or flash 206B, and second reflective surface 612 over imaging sensor 208. In other examples, alignment feature 306 may be received in an opening on device 204, such as a speaker opening or an earphone jack.

Figure 7:
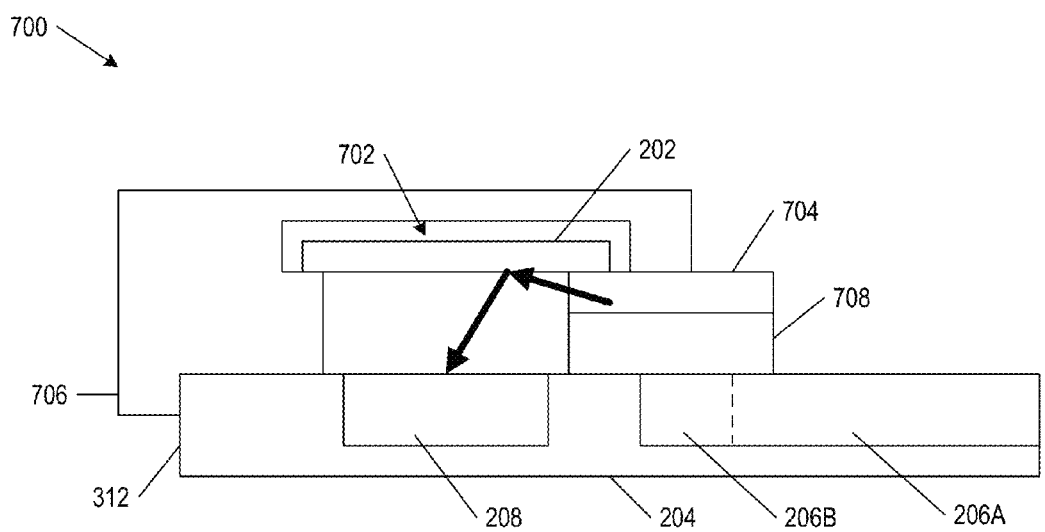
FIG. 7 shows a side view of a fifth test strip peripheral device for portable computing devices in examples of the present disclosure.

FIG. 7 shows a peripheral device 700 for device 204 in examples of the present disclosure. Peripheral device 700 includes a test strip slot or compartment 702 to receive test strip 202, a light guide 704 to direct light to the reaction area on the test strip, and an alignment feature 706 to aid the placement of the peripheral device on the portable computing device. When flash 206B is used as the light source, peripheral device 700 includes a color filter 708 to control the color of the light illuminating the reaction area on test strip 202.

Light is emitted upward from screen 206A or flash 206B, optionally travels through color filter 708, scatters within light guide 704, reflects diagonally downward from the reaction area on test strip 202, and impinges image sensor 208.

Light guide 704 is a block of scattering material, such as an acrylic, polycarbonate, epoxy, or glass with doped hollow shells, located above a portion of screen 206A or flash 206B and adjacent to test strip 202 in test strip slot 702. Light guide 704 may be covered in a case or by a coating to prevent ambient light from entering so the reaction area on test strip 202 is illuminated substantially by screen 206A or flash 206B.

Color filter 708 is located over a portion of screen 206A or flash 206B.

Alignment feature 706 abuts against edge 312 of device 204 to place light guide 704 over a portion of screen 206A or flash 206B, and test strip 202 over imaging sensor 208. In other examples, alignment feature 306 may be received in an opening on device 204, such as a speaker opening or an earphone jack.

Figure 8A:
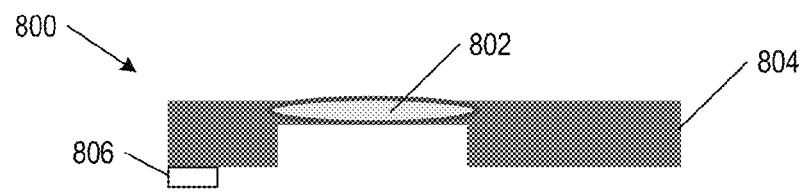
FIGS. 8A and 8B show side and top views of a sixth test strip peripheral device for portable computing devices in examples of the present disclosure.
Figure 8B:
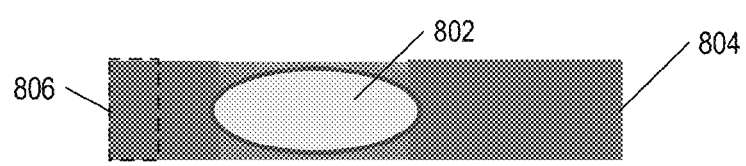

FIGS. 8A and 8B shows an integral test strip peripheral device 800 for device 204 (FIG. 2A or 2B) in examples of the present disclosure. Peripheral device 800 includes a test strip 802 integrated with a light guide 804 and an alignment feature 806. Light guide 804 directs light from screen 206A or flash 206B (FIG. 2A or 2B) to a reaction area on test strip 802. Light guide 804 may be covered in a case or by a coating to prevent ambient light from entering so the reaction area on test strip 202 is illuminated substantially by screen 206A or flash 206B.

Alignment feature 806 abuts against an edge of device 204 to place light guide 804 over a portion of screen 206A or flash 206B, and test strip 802 over imaging sensor 208 (FIGS. 2A and 2B). In other examples, alignment feature 306 may be received in an opening on device 204, such as a speaker opening or an earphone jack.

Figure 9:
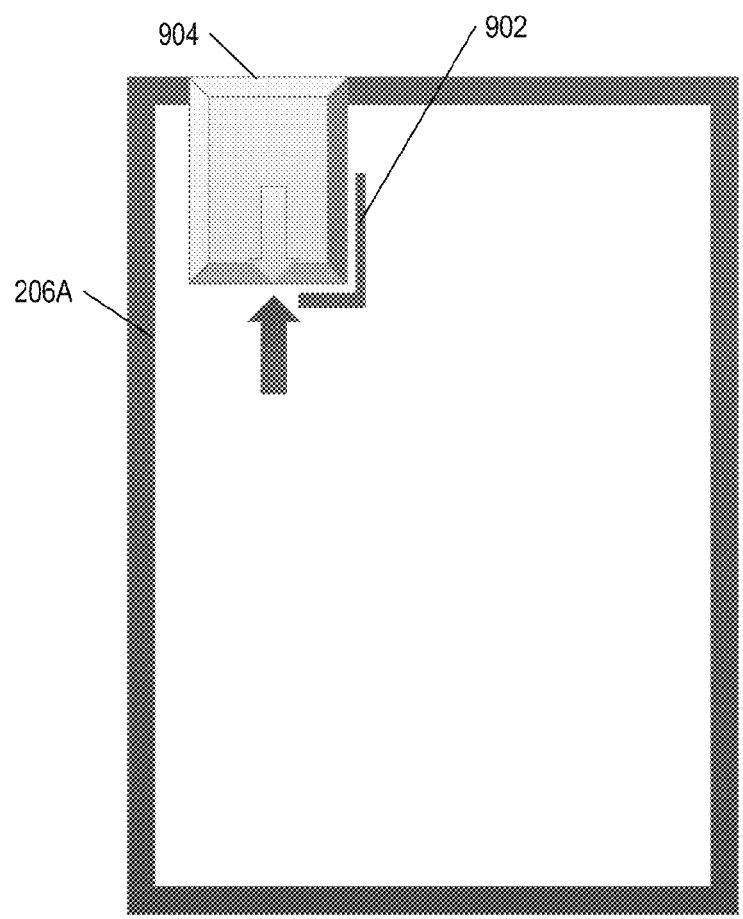
FIG. 9 shows the screen of a portable computing device with an alignment mark to facilitate the placement of a test strip peripheral device in examples of the present disclosure.

FIG. 9 shows screen 206A of device 204 (FIG. 2A or 2B) in examples of the present disclosure. An alignment mark 902 is generated on screen 206A to facilitate the placement of a test strip peripheral device 904 on device 204.

In some examples, alignment mark 902 is used to properly align the peripheral device in two dimensions (e.g., X and Y dimensions). In other examples, alignment mark 902 work in conjunction with an alignment feature of peripheral device 904. The alignment feature may abut against an edge of device 204 or insert into an opening on the portable computing device, such as a speaker opening or an earphone jack. The alignment feature may align peripheral device 904 in one dimension (e.g., the Y dimension) while alignment mark 902 may align the peripheral device in another dimension (e.g., the X dimension).

FIGS. 10A, 10B, and 10C show test strips with reaction and reference areas in examples of the present disclosure. A reference area is used to determine imaging conditions, such as exposure time, f-stop, and film speed. Based on the color and the color intensity of the reference area, processor 214

(FIG. 2A or 2B) executing application 212 (FIG. 2A or 2B) may select the imagining conditions. The reference area may be a color chart, a gray card, or a pure white or black zone.

In FIG. 10A, a test strip 1000A has a reaction area 1002 and a reference area 1004A adjacent to the reaction area in examples of the present disclosure. In FIG. 10B, a test strip 1000B has reaction area 1002 and a reference area 1004B that surrounds the reaction area in examples of the present disclosure. In FIG. 10C, a test strip 1000C has reaction area 1002 and a reference area 1004C that is surrounded by the reaction area in examples of the present disclosure.

FIGS. 11A, 11B, and 11C show test strips with reaction and color calibration areas in examples of the present disclosure. A color calibration area is used to characterize the illumination provided by a particular screen and adjust an analyte measurement accordingly. The color calibration area may be a color chart, a gray card, or a purely black or white zone.

In FIG. 11A, a test strip 1100A has a reaction area 1102 and a color calibration area 1104A that is a color chart arranged as a strip in examples of the present disclosure. In FIG. 11B, a test strip 1100B has reaction area 1102 and a color calibration area 1104B that is a gray chart arranged as a strip. In FIG. 11C, a test strip 1100C has reaction area 1102 and a color calibration area 1104C in a concentric configuration in examples of the present disclosure.

FIG. 12A shows a test strip or a test strip peripheral device 1202 with conductive smart dots 1204 in examples of the present disclosure. Smart dots 1204 are areas that have a different conductive property than the rest of the test strip or peripheral device 1202 so they can be detected by a touchscreen on a portable computing device.

FIG. 12B shows smart dots 1204 that are made of conductive rubber in examples of the present disclosure. FIG. 12C shows smart dots 1204 that are made of conductive fibers in examples of the present disclosure. FIG. 12D shows smart dots 1204 that are made of conductive cloth in examples of the present disclosure. FIG. 12E shows smart dots 1204 that are made of a combination of metal and plastic in examples of the present disclosure.

FIGS. 13A, 13B, and 13C show different arrangements (i.e., patterns) of smart dots 1204 on test strip or peripheral device 1202 in examples of the present disclosure. When smart dots 1204 contact a touchscreen on a portable computing device, such as touchscreen 206A on device 204 (FIG. 2A or 2B), the portable computing device can detect the smart dots. The different arrangements of smart dots 1204 may encode the analyte type, the product batch number of test strip or peripheral device 1202, or both. The orientation of smart dots 1204 may also convey the location and the orientation of the reaction area on test strip or peripheral device 1202.

Alternatively smart dots 1204 are not conductive but form a visible code on test strip or peripheral device 1202. Such a code 1204 is captured in an image along with the reaction area and decoded by processor 214 (FIG. 2A or 2B) to reveal an analyte type, a product batch number of test strip or peripheral device 1202, or both. The orientation of code 1204 may also convey the location and the orientation of the reaction area on test strip or peripheral device 1202.

Figure 14A:
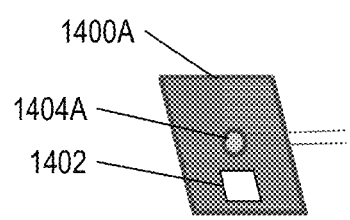
FIG. 14A shows a test strip with a reaction area and a temperature sensor in examples of the present disclosure.

FIG. 14A shows a test strip 1400A with a reaction area 1402 and a temperature sensor 1404A in examples of the present disclosure. A portable computing device, such as device 204 (FIG. 2A or 2B), can electronically read temperature sensor 1404A and compensate the analyte measurement based on the temperature. Temperature sensor 1404A may be a thermistor or a resistance temperature detector with a transmitter. Device 204 includes a receiver to read temperature sensor 1404A using near field communication (NFC).

Figure 14B:
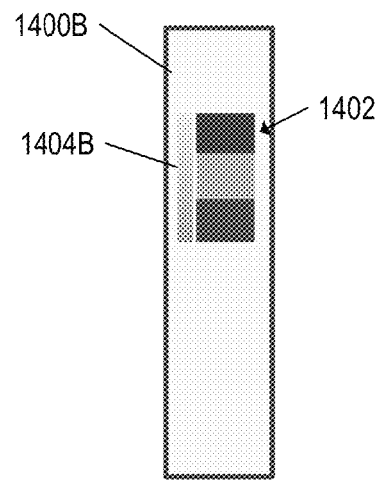
FIG. 14B shows a test strip with reaction and temperature indication areas in examples of the present disclosure.

FIG. 14B shows a test strip 1400B with reaction area 1402 and a temperature indication area 1404B in examples of the present disclosure. A portable computing device, such as device 204 (FIG. 2A or 2B), can optically read temperature indication area 1404B and compensate the analyte measurement based on the temperature.

Figure 15:
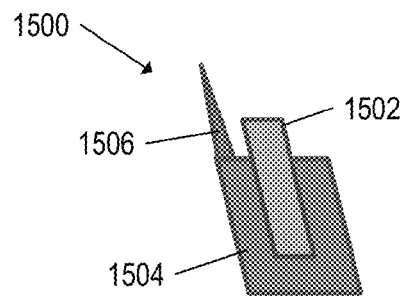
FIG. 15 shows a seventh test strip peripheral device for portable computing devices in examples of the present disclosure.

FIG. 15 shows a test strip or a test strip peripheral device 1500 for device 204 (FIG. 2A or 2B) in examples of the present disclosure. Test strip or peripheral device 1500 includes a test strip 1502, a light guide 1504 to direct light to a reaction area on the test strip, and an integral lancet 1506.

Figure 16:
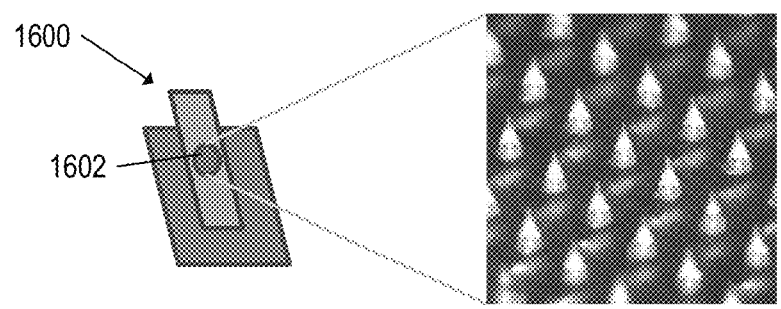
FIG. 16 shows an eighth test strip peripheral device for portable computing devices in examples of the present disclosure.
Figure 17A:
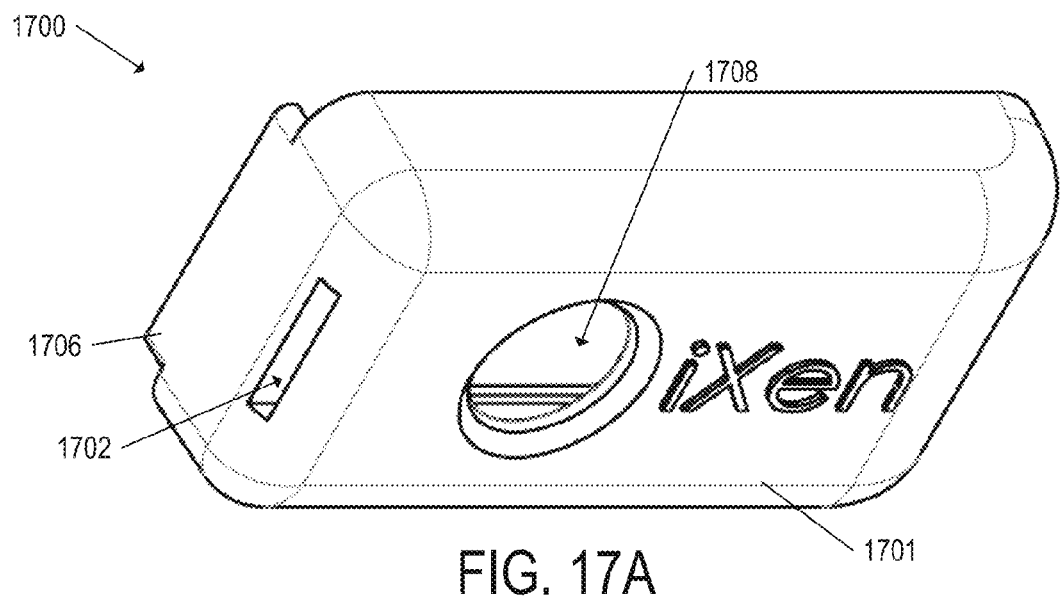
FIGS. 17A, 17B, 17C, and 17D show perspective, top, bottom, and side views of a ninth test strip peripheral device in examples of the present disclosure.
Figure 17B:
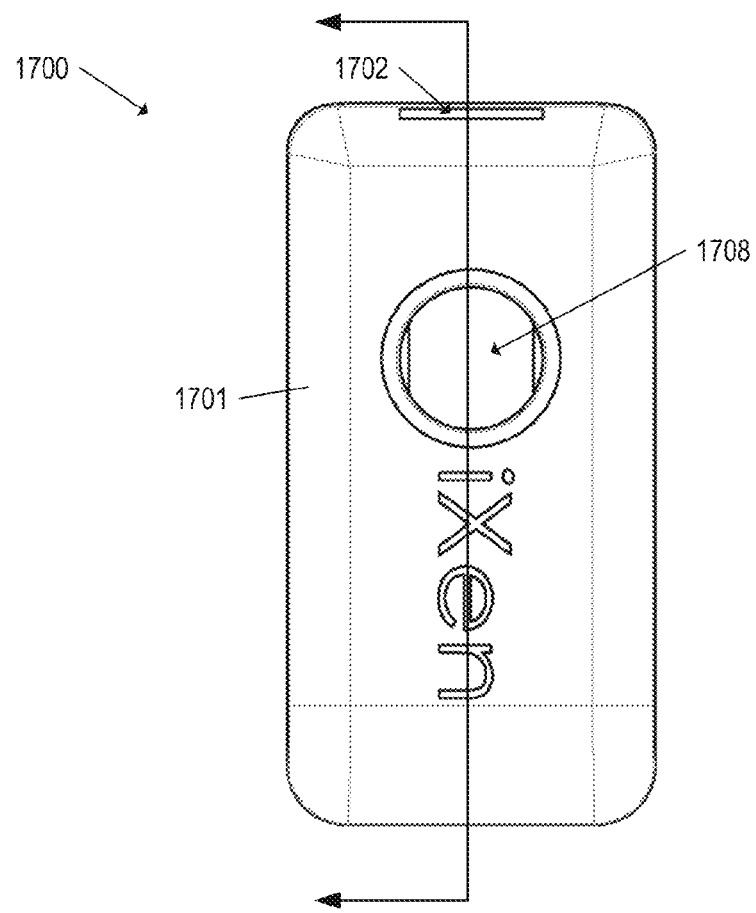
Figure 17C:
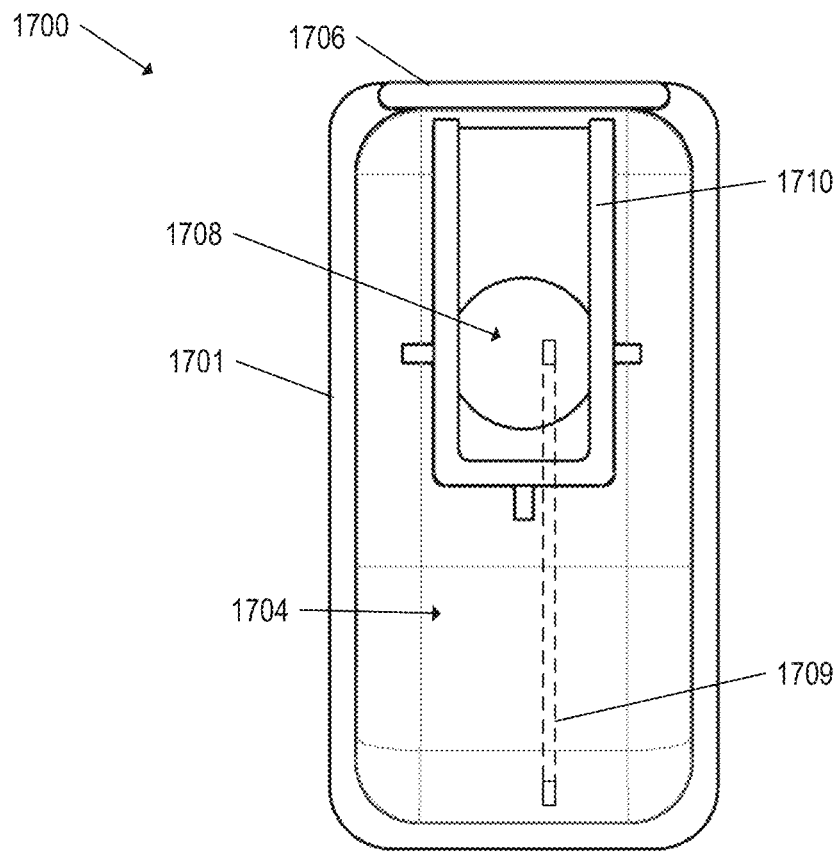
Figure 17D:
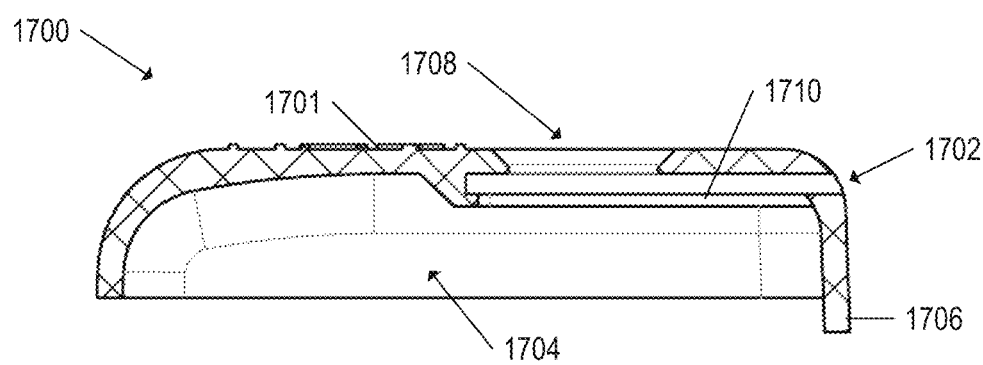

FIG. 16 shows a test strip or a test strip peripheral device 1600 for device 204 (FIG. 2A or 2B) in examples of the present disclosure. Test strip or peripheral device 1600 includes a lancet 1602 that is a microneedle array.

FIGS. 17A, 17B, 17C, and 17D show perspective, top, bottom, and side views of a test strip peripheral device 1700 in examples of the present disclosure. Peripheral device 1700 includes a hollow case 1701 with a slot 1702 to receive a test strip, a reflective interior 1704 (FIGS. 17C and 17D) that forms a light guide to direct light to a reaction area on the test strip, and an alignment feature 1706 (e.g., a lip of the case shown in FIGS. 17C and 17D) to aid the placement of the peripheral device on device 204 (FIG. 2A or 2B). Case 1701 has an open bottom exposed to a portion of screen 206A or flash 206B (FIG. 2A or 2B) and image sensor 208 (FIG. 2A or 2B). Case 1701 may have a top opening 1708 for a user to deposit a specimen sample on the reaction area of the test strip. In other examples, case 1701 does not have top opening 1708 and the user deposits the specimen sample through an end of the test strip exposed from peripheral device 1700. The test strip has a capillary path that carries the specimen sample from the exposed end to the reaction area. In yet other examples, peripheral device 700 includes a capillary 1709 (e.g., shown in phantom in case 1701 of FIG. 17C) that carries the specimen sample to the to the reaction area inside case 1701. Capillary 1709 may have a first opening at one end of case 1701, a conduit that travels along the thickness of the case, and a second opening to the interior of the case above the reaction area. In these examples, the reaction area on the test strip is illuminated substantially by screen 206A or flash 206B as the reaction area is enclosed within case 1701 and not exposed to ambient light. Within case 1701, the test strip is supported by a U-shaped guide 1710.

Figure 18:
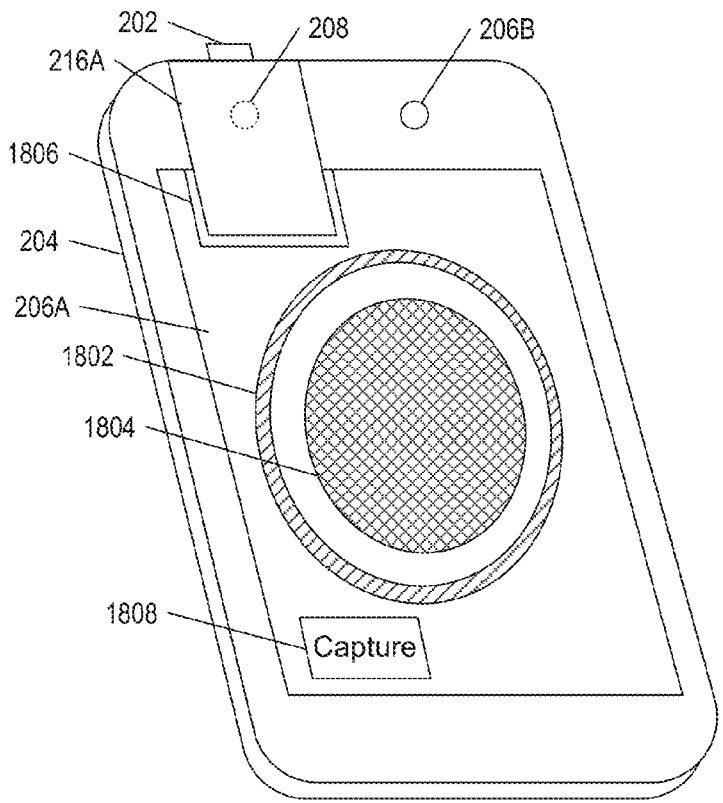
FIG. 18 shows the screen of a portable computing device in examples of the present disclosure.

FIG. 18 shows screen 206A of device 204 in examples of the present disclosure. Screen 206A displays a live preview of what image sensor 208 (shown in phantom) will capture. A boundary 1802 is displayed on screen 206A to indicate where to locate a reaction area 1804 of test strip 202 by adjusting the placement of peripheral device 216A on device 204. In examples where screen 206A serves as a light source, a portion 1806 of screen 206A emits light to illuminate the reaction area on test strip 202. In these examples, portion 1806 may also server as alignment marker 902 (FIG. 9) to facilitate the placement of peripheral device 216A on device 204. In other examples, a separate alignment marker 902 is provided on screen 206A. Screen 206A displays a capture button 1808 to accept an input command for image sensor 208 to capture reaction area 1804.

Figure 19:
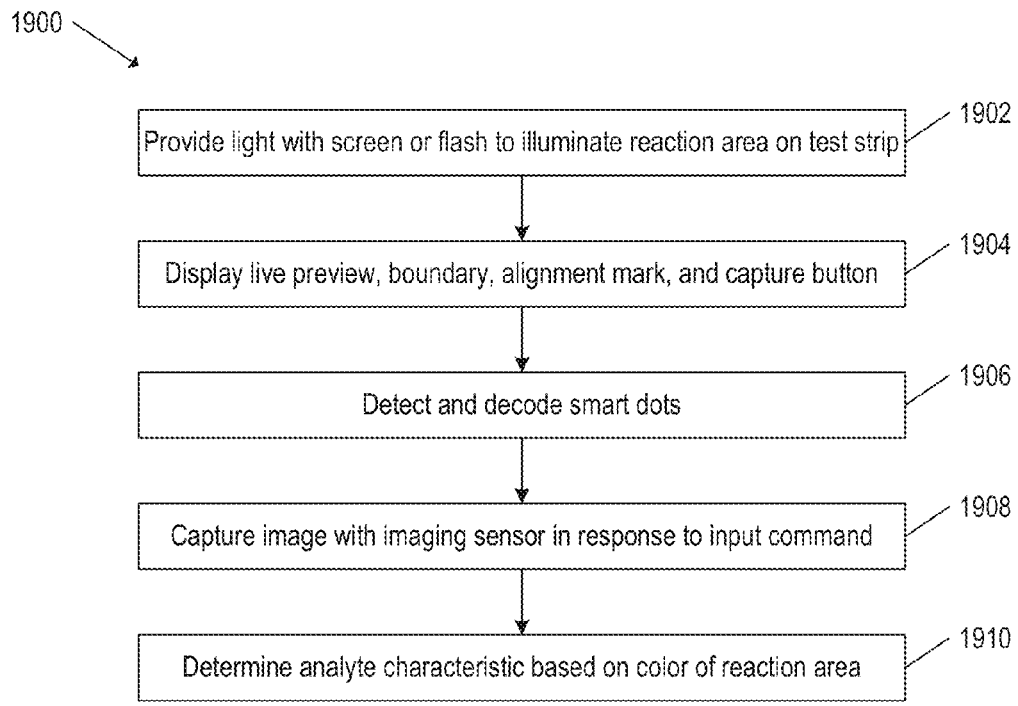
FIG. 19 is a flowchart of a method for a portable computing device to read a test strip in a test strip peripheral device placed on the portable computing device in examples of the present disclosure.

FIG. 19 is a flowchart of a method 1900 for device 204 (FIG. 2A or 2B) to read the reaction area on test strip 202 (FIG. 2A or 2B), which is located in test strip peripheral device 216A or 216B (FIG. 2A or 2B) placed over image sensor 208 (FIG. 2A or 2B) and a portion of screen 206A or flash 206B, in examples of the present disclosure. Method 1900 may be implemented by processor 214 (FIG. 2A or 2B) executing application 212 (FIG. 2A or 2B). Although blocks for method 1900 are illustrated in a sequential order, these blocks may also be performed in parallel, and/or in a different order than those described herein. Also, the various blocks may be combined into fewer blocks, divided into additional blocks, and/or eliminated based upon the desired implementation. Method 1900 may begin in block 1902.

In block 1902, processor 214 provides light with screen 206A or flash 206B to illuminate the reaction area on test strip 202. Peripheral device 216A or 216B directs light from screen 206A or flash 206B, respectively, to the reaction area. In examples where screen 206A is used as a light source, processor 214 uses portion 1806 (FIG. 18) on the screen to illuminate the reaction area. In these examples, portion 1806 may also serve as alignment marker 902. Block 1902 may be followed by block 1904.

In block 1904, processor 214 displays a live preview of what image sensor 208 will capture on screen 206A. Processor 214 also displays boundary 1802 (FIG. 18) on screen 206A to indicate where to locate the reaction area of test strip 202 by adjusting the placement of peripheral device 216A or 216B on device 204. Processor 214 further displays capture button 1808 (FIG. 18) to receive an input command to capture an image of the reaction area on test strip 202. Processor 214 may display alignment marker 902 (FIG. 9) on screen 206A for peripheral device 216A or 216B. Block 1904 may be followed by block 1906.

In block 1906, touchscreen 206A senses any smart dots on test strip 202 or peripheral device 216A or 216B that are contacting the screen. Based on the arrangement of the smart dots, processor 214 may determine an analyte type, a production batch number of the test strip, or both. Based on the location and the orientation of the smart dots, processor 214 may more accurately determine the location and the orientation of the reaction area on test strip 202. Processor 214 may also electronically read temperature sensor 1404A (FIG. 14A) if present. Block 1906 may be followed by block 1908.

In block 1908, processor 214 captures an image with image sensor 208 in response to an input command (e.g., a selection of capture button 1808). When test strip 202 includes a reference area, processor 214 may first determine imaging conditions based on the reference area before capturing the image.

The image includes the reaction area. The image may also include a color calibration area, a temperature indication area, or both. Block 1908 may be followed by block 1910.

In block 1908, processor 214 determines an analyte characteristic based on the color of the captured reaction area in the image. When the image includes a color calibration area, processor 214 may determine the color of the reaction area based on the color calibration area. Processor 214 may correct the analyte characteristic based on a temperature detected by a temperature indication area or a temperature sensor. When the image includes a temperature indication area, processor 214 determines the temperature based on the color of the temperature indication area.

When processor 214 is able to determine the characteristic of multiple analyte types, the processor may first determine the analyte type based on the smart dots on a test strip or a peripheral device. When processor 214 is able to correct the analyte characteristic based on a production batch number, which may be obtained through a software update over the Internet, the processor may first determine the product batch number based on the smart dots on the test strip or the peripheral device.

In some examples, processor 214 repeats method 1900 for a different illumination intensity or color. Specifically, processor 214 may change the intensity or color of portion 1806 on screen 206A and capture another image of the reaction area under a different illumination intensity or color. Using two illumination colors extends the dynamic range of the measurement.

For example, one image is captured under one illumination intensity or color to enhance the details for detecting lower concentrations, and another image is captured under a different illumination intensity or color to enhance the details for detecting higher concentrations. From the two images, processor 214 may select one image based that has average RGB values of the captured reaction area that is neither too low (e.g., <30) or too high (e.g., >240). Processor 214 then correlates the color of the captured reaction area to the analyte characteristic.

Figure 20:
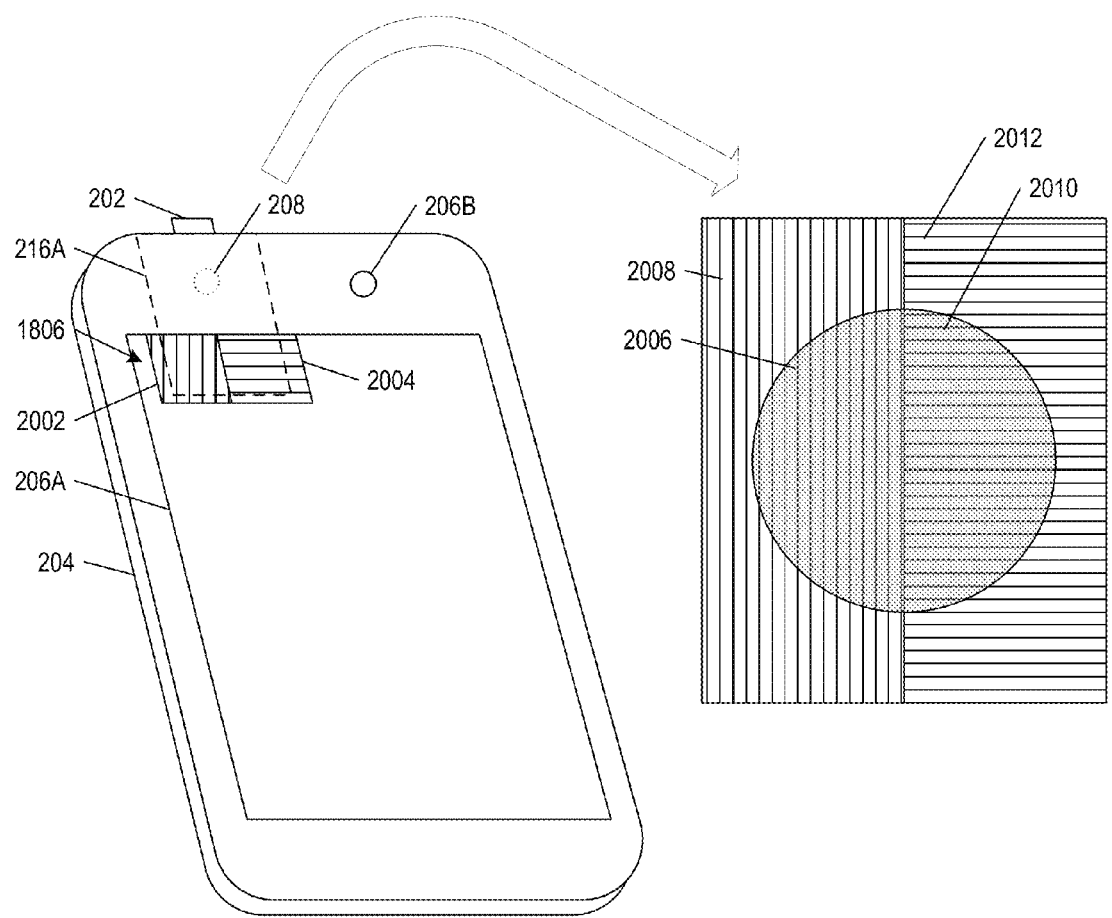
FIG. 20 shows the screen of a portable computing device in examples of the present disclosure.

Instead of repeating method 1900, processor 214 may split portion 1806 into parts 2002 and 2004 of different intensities or colors as shown in FIG. 20 in examples of the present disclosure. Thus a first part 2006 of the reaction area is illuminated by light 2008 of a first intensity or color, and a second part 2008 of the reaction area is illuminated by light 2010 of a second intensity or color 2012. Processor then determines the analyte characteristic based on the captured two parts in the image. In some examples, processor 214 selects one captured part in the image that has average RGB values that is neither too low or too high, and correlates the color of that captured part to the analyte characteristic. In other examples, processor 214 calculates the average or median values RGB values of the two captured parts combined and determines the analyte characteristic based on the average or median RGB values. In yet other examples, processor 214 calculates the average or median values RGB values of each captured part and determines the analyte characteristic based on the average or median RGB values of both captured parts.

FIGS. 21A, 21B, 21C, and 21D show first perspective, second perspective, top, bottom, and side views of a test strip peripheral device 2100 in examples of the present disclosure. Peripheral device 2100 includes a case 2101 with a compartment 2102 to receive a test strip, a reflective interior 2104 (FIG. 21D) that forms a light guide to direct light to a reaction area on the test strip, and an alignment feature 2106 (FIG. 21D) to aid the placement of the peripheral device on device 204 (FIG. 2A or 2B). Case 2101 has a hollow body 2108 and a lid 2110 hinged to the body. Body 2108 has an open bottom exposed to a portion of screen 206A or flash 206B (FIG. 2A or 2B) and image sensor 208 (FIG. 2A or 2B). Compartment 2102 is formed by a recessed area on the top of body 2108. Recessed area 2102 defines an opening 2112 to expose the reaction area of the test strip to imaging sensor 208.

Lid 2110 has a top opening 2114 for a user to deposit a specimen sample on the reaction area on the test strip. In other examples, lid 2110 does not have top opening 2114 and the user deposits the specimen sample through an end of the test strip exposed from peripheral device 2100. The test strip has a capillary path that carries the specimen sample from the exposed end to the reaction area. In yet other examples, peripheral device 2100 includes a capillary 2116 (e.g., shown in phantom in lid 2110 of FIG. 21C) that carries the specimen sample to the to the reaction area inside case 2101. Capillary 2116 may have a first opening at one end of case lid 2110, a conduit that travels along the thickness of the lid, and a second opening to the interior of the lid above the reaction area. In these examples, the reaction area on the test strip is illuminated substantially by screen 206A or flash 206B as the reaction area is enclosed within case 2101 and not exposed to ambient light.

The features of the test strip peripheral devices and the test strips may be combined. For example, a test strip peripheral device may include any combination of a light guide, an alignment feature, a lancet, and smart dots. Similarly a test strip may include any combination of a reaction area, a reference area, a color calibration area, a temperature sensor, a temperature indication area, and smart dots.

The systems and methods disclosed herein may be used to test for the presence and/or concentration of certain analytes, such as but not limited to glucose, cholesterol, uric acid, troponin I, ketone, protein, nitrite and leukocyte. Various fluids may be tested, such as but not limited to blood, interstitial fluid, urine, saliva, and other bodily fluids.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method for a portable computing device having an image sensor and a screen on a same side of the portable computing device to read a reaction area on a test strip, which is located in a peripheral device, the method comprising:
   providing light with a portion of the screen to the peripheral device, which is placed over the image sensor and the portion of the screen and directs the light from the portion of the screen to illuminate the reaction area in a manner that the image sensor on the same side is impinged by the light passing through the reaction area or by the light scattered or reflected from the reaction area;
   capturing an image with the image sensor substantially free from ambient light, wherein the image includes the reaction area; and
   determining an analyte characteristic based on a color of the captured reaction area in the image.

2. The method of claim 1, wherein the screen comprises a touchscreen.

3. The method of claim 2, wherein the portable computing device comprises a smart phone or a tablet computer.

4. The method of claim 1, further comprising:
   displaying on the screen a boundary within which to locate the reaction area by adjusting a placement of the peripheral device on the portable computing device; and
   displaying on the screen a live preview of what the image sensor will capture.

5. The method of claim 1, further comprising displaying on the screen an alignment marker for the peripheral device.

6. The method of claim 1, wherein the test strip includes a reference area and, prior to capturing the image including the reaction area, the method further comprises:
   determining an imaging condition based on the reference area; and
   adjusting an image sensor setting based on the imaging condition.

7. The method of claim 6, wherein the reference area is a color chart, a gray card, or a purely black or white zone, and the imaging condition is a shutter speed, an f-stop, or a film speed.

8. The method of claim 1, wherein the test strip includes a color calibration area, the image includes the color calibration area, and the method further comprises determining the color of the captured reaction area based on the captured color calibration area in the image.

9. The method of claim 8, wherein the color calibration area is a color chart, a gray card, or a purely black or white zone.

10. The method of claim 1, further comprising:
    changing the portion of the screen to a different color; and
    capturing another image including the reaction area, wherein determining an analyte characteristic is further based on another color of the captured reaction area in the other image.

11. The method of claim 1, wherein the screen includes a touchscreen, and the method further comprises sensing areas on the test strip or the peripheral device contacting the screen.

12. The method of claim 11, further comprising:
    determining an arrangement of the areas, an orientation of the areas, or a combination thereof; and
    based on the arrangement of the areas, the orientation of the areas, or the combination thereof, determining an analyte type, a production batch number of the test strip, an orientation of the reaction area on the test strip, or a combination thereof.

13. A method for a portable computing device to read a reaction area on a test strip, which is located in a peripheral device placed over an image sensor and a touchscreen of the portable computing device, the method comprising:
    sensing areas on the test strip or the peripheral device contacting the touchscreen, wherein the areas comprises conductive dots made of conductive rubber, conductive fiber, conductive cloth, or a combination thereof;
    determining an arrangement of the areas, an orientation of the areas, or a combination thereof;
    based on the arrangement of the areas, the orientation of the areas, or the combination thereof, determining an analyte type, a production batch number of the test strip, an orientation of the reaction area on the test strip, or a combination thereof;
    providing light with a portion of the touchscreen of the portable computing device, wherein the peripheral device directs light from the touchscreen to the reaction area;
    capturing an image with the image sensor, wherein the image includes the reaction area; and
    determining an analyte characteristic based on a color of the captured reaction area in the image.

14. The method of claim 1, wherein:
    the test strip or the peripheral device includes a visible code;
    the image includes the code; and
    the method further comprises determining an analyte type, a production batch number of the test strip, an orientation of the reaction area on the test strip, or a combination thereof based on the captured code.

15. The method of claim 1, wherein the test strip includes a temperature sensor, and the method further comprises:
    electrically reading the temperature sensor to determine a temperature of the test strip; and correcting the analyte characteristic based on the temperature of the test strip.

16. The method of claim 1, wherein the test strip includes a temperature indication area, the image further includes the temperature indication area, and the method further comprises correcting the specimen characteristic based on the captured temperature indication area in the image.

17. The method of claim 1, wherein the portion of the screen includes at least a first part of a first intensity or a first color and a second part of a second intensity or a second color, and determining an analyte characteristic comprises determining the analyte characteristic based on colors or intensities of the first part and the second part of the captured reaction area in the image.

18. A method for a portable computing device having an image sensor and a screen on a same side of the portable computing device to read a reaction area on a test strip, which is located in a peripheral device, the method comprising:

providing light with a portion of the screen to the peripheral device, which is placed over the image sensor and the portion of the screen and directs the light from the portion of the screen to illuminate the reaction area in a manner that the image sensor on the same side receives the light passing through the reaction area or the light scattered or reflected from the reaction area;

prior to capturing the image including the reaction area, determining an imaging condition based on a reference area on the test strip;

adjusting an image sensor setting based on the imaging condition;

capturing an image with the image sensor substantially free from ambient light and based on the image sensor setting, wherein the image includes the reaction area; and determining an analyte characteristic based on a color of the captured reaction area in the image.

* * * * *